United States Patent
Zhang et al.

(10) Patent No.: US 12,109,337 B2
(45) Date of Patent: Oct. 8, 2024

(54) DEGRADABLE ZINC BASE ALLOY IMPLANT MATERIAL AND PREPARATION METHOD AND USE THEREOF

(71) Applicants: Shandong Rientech Medical Tech Co., Ltd., Dezhou (CN); Luning Wang, Beijing (CN)

(72) Inventors: Haijun Zhang, Dezhou (CN); Luning Wang, Beijing (CN); Chao Zhou, Beijing (CN); Yuxia Yin, Dezhou (CN); Shoutao Lu, Dezhou (CN); Yanwei Zhao, Dezhou (CN)

(73) Assignees: SHANDONG RIENTECH MEDICAL TECH CO., LTD., Dezhou (CN); Luning Wang, Beijing (CN)

( * ) Notice: Subject to any disclaimer, the term of this patent is extended or adjusted under 35 U.S.C. 154(b) by 711 days.

(21) Appl. No.: 16/083,009

(22) PCT Filed: Mar. 10, 2017

(86) PCT No.: PCT/CN2017/076307
§ 371 (c)(1),
(2) Date: Sep. 7, 2018

(87) PCT Pub. No.: WO2017/152878
PCT Pub. Date: Sep. 14, 2017

(65) Prior Publication Data
US 2019/0083685 A1    Mar. 21, 2019

(30) Foreign Application Priority Data
Mar. 10, 2016 (WO) ............... PCT/CN2016/076066

(51) Int. Cl.
*A61L 31/14* (2006.01)
*A61L 27/04* (2006.01)
(Continued)

(52) U.S. Cl.
CPC ............. *A61L 31/148* (2013.01); *A61L 27/04* (2013.01); *A61L 27/047* (2013.01); *A61L 27/58* (2013.01);
(Continued)

(58) Field of Classification Search
None
See application file for complete search history.

(56) References Cited

U.S. PATENT DOCUMENTS

2008/0195170 A1    8/2008  Asgari
2017/0028107 A1*   2/2017  Zhou ...................... C22C 18/00
(Continued)

FOREIGN PATENT DOCUMENTS

CN    101147813 A         3/2008
CN    102766780 A    *   11/2012
(Continued)

OTHER PUBLICATIONS

English Machine Translation of CN-104689378-A (Year: 2015).*
(Continued)

*Primary Examiner* — Paul A Wartalowicz
*Assistant Examiner* — Catherine P Smith
(74) *Attorney, Agent, or Firm* — Scully, Scott, Murphy & Presser, P.C.

(57) ABSTRACT

Disclosed is a degradable zinc base alloy implant material comprising, by mass percentage content, 0.01 wt % to 14 wt % of Fe, 0 wt % to 13 wt % of functional elements and the remainder being Zn and a preparation method and use thereof. During preparation, Zn, Fe, and the functional elements are homogeneously mixed and placed into a high-purity graphite crucible and smelted together under a mixed gas atmosphere of $SF_6$ and $CO_2$. The mechanical properties of the zinc base alloy implant material have been significantly improved, so that the implant material is easy to (Continued)

process and shape, and so that the properties of strength and plasticity, etc., meet the basic requirements of human body implant materials, such as vascular stents, orthopedic internal fixation systems, and the like.

2 Claims, 2 Drawing Sheets

(51) Int. Cl.
    *A61L 27/58*     (2006.01)
    *A61L 31/02*     (2006.01)
    *A61L 31/10*     (2006.01)
    *A61L 31/16*     (2006.01)
    *C22C 18/00*     (2006.01)
    *C22C 18/02*     (2006.01)
    *C22F 1/16*     (2006.01)

(52) U.S. Cl.
    CPC ............. *A61L 31/022* (2013.01); *A61L 31/10* (2013.01); *A61L 31/16* (2013.01); *C22C 18/00* (2013.01); *C22C 18/02* (2013.01); *C22F 1/165* (2013.01); *A61L 2300/216* (2013.01); *A61L 2300/416* (2013.01); *A61L 2420/02* (2013.01); *A61L 2420/06* (2013.01)

(56) References Cited

U.S. PATENT DOCUMENTS

2017/0218483 A1*   8/2017   Huang ...................... A61F 2/82
2019/0008996 A1*   1/2019   Zhang .................. A61L 27/427

FOREIGN PATENT DOCUMENTS

| | | | | |
|---|---|---|---|---|
| CN | 103736152 A | | 4/2014 | |
| CN | 104328312 A | * | 2/2015 | |
| CN | 104587532 A | | 5/2015 | |
| CN | 104651664 A | * | 5/2015 | ............. A61L 31/02 |
| CN | 104689369 A | * | 6/2015 | ............. A61L 17/00 |
| CN | 104689378 A | * | 6/2015 | ............. A61L 27/04 |
| CN | 105063427 A | | 11/2015 | |
| WO | 2015139355 A1 | | 9/2015 | |

OTHER PUBLICATIONS

English Machine Translation of CN 104689369 A (Year: 2015).*
D. Vojtch, J. Kubásek, J. Šerák, P. Novák, Mechanical and corrosion properties of newly developed biodegradable Zn-based alloys for bone fixation, Acta Biomaterialia, vol. 7, Issue 9, 2011, pg. pp. 3515-3522 (Year: 2011).*
English Machine Translation of CN 102766780 A (Year: 2012).*
English Machine Translation of CN-104651664-A (Year: 2015).*
CN-104328312-A English Machine Translation (Year: 2015).*
CN-104689369-A English machine translation (Year: 2015).*
Supplementary Partial European Search Report dated Jul. 23, 2019 received in European Application No. 17 76 2564.7.
Mita K. et al., "Phase Diagram Study of Fe—Zn Intermetallics", Journal of Phase Equilibria 22(2):122-125 (Apr. 2001).
International Search Report dated Jun. 9, 2017 issued in PCT/CN2017/076307.
Extended European Search Report dated Oct. 25, 2022 received in European Application No. 22179866.3, 7 pages.

* cited by examiner

DEGRADABLE ZINC BASE ALLOY IMPLANT MATERIAL AND PREPARATION METHOD AND USE THEREOF

FIELD OF THE INVENTION

The present invention relates to the technical field of medical device technology, and in particular to a degradable zinc base alloy implant material, as well as a preparation method and use thereof.

BACKGROUND OF THE INVENTION

Implanted medical devices refer to medical devices that are introduced fully or partially into the human body, body cavities, tracts, or mouth by means of surgical operation, or used to replace epithelial surface or ocular surface of human body, and are retained in the human body for 30 days (inclusive) or longer after the surgical operation is finished, or that are absorbed by the human body. Implanted medical devices belong to high-risk medical devices (category III) because they directly contact with the internal tissues of the human body and the contact time is relatively long. Implanted medical devices are applied more and more widely and have been developed into a market with tens of billions in yuan market value as the population of China becomes older and as medical technology develops.

The implant materials used for implanted medical devices may be categorized by composition into metal materials, macromolecular materials, ceramic materials, natural materials, and composite materials composed of two or more types of the aforementioned materials. Among those, metal materials are applied very widely, especially in implanted medical devices that must have a specific load bearing performance, such as orthopedic implants, prosthodontic implants, and cardiovascular implants, etc., owing to the outstanding mechanical properties of metal materials.

In traditional applications, to avoid adverse reactions between implant materials and the human body, metal materials that have higher corrosion resistance property and inertia (e.g., pure titanium, stainless steel, cobalt base alloys, or titanium base alloys, etc.) are preferred in the selection of metal materials. However, such materials with high inertia usually take a temporary role after being implanted into human body, and may become a burden to the patient after the pathological stage has concluded, because they may result in secondary operations and long-term risks. Typically, for example, nails and/or plate materials for internal fracture fixation (made of stainless steel, Co—Cr—Mo alloy, or titanium/titanium alloy, etc.) have to be taken out through a secondary operation after the broken bones have knitted; besides, since the difference in elastic modulus between such an inert material and the human skeleton is too great, a stress shielding effect exists and, consequently, side effects such as delayed bone knitting and mismatching, etc., may occur. For another example, once metal stents (made of 316L stainless steel or cobalt base alloys, etc.) for coronary intervention are implanted into the body of a patient, the patient will have to carry the metal stents and take anticoagulant drugs for his/her entire life, and cannot undergo normal MRI examination anymore; in addition, there is a risk of slow release of metal ions into the body, hyperplasia proliferation, and adverse cardiac events over the long term.

With the development of material science, degradable polymeric materials have gradually received attention as implant materials. Presently, degradable polymers (polylactide and polycarbonate, etc.) have been applied preliminarily in some products where the mechanical property requirements are lower, (in domains such as peripheral vascular stents, or in maxillofacial/hand and foot fracture regions, etc.). However, the scope of application of degradable polymeric materials has always been quite limited, owing to problems with the mechanical properties of these materials.

Efforts have been made to replace traditional "inert" metal materials and polymeric materials with degradable metal materials in order to overcome the drawbacks mentioned above. Research in this area has mainly focused on magnesium (Mg) and iron (Fe), which are essential metal elements in the human body and have relatively good mechanical properties. Because the environment of the human body is rich in chloride ions (Cl), magnesium and iron may react and generate an oxide film. These oxide films are loose and porous, and can't provide effective protection for the metal material substrate; moreover, magnesium (Mg) has a higher standard equilibrium electrode potential and exhibits higher degradation activity, while iron has a lower standard equilibrium electrode potential and exhibits lower degradation activity.

To overcome the performance drawbacks of materials made of a single metal element, the focus of research has been on alloys based on a metal element A, which are formed by utilizing the metal element A as a base material and adding other metal elements to the metal element A. However, it is found in the actual development process that although the mechanical properties of a magnesium base alloy can meet clinical requirements in the initial period after implantation, the mechanical properties become compromised too quickly to meet the clinical requirements for load bearing capacity retention time of the material, owing to the extremely high degradation rate of magnesium. At present, a magnesium alloy "JDBM", of which the degradation rate is controlled at a relatively ideal level, has corrosion resistance close to that of high-purity magnesium, i.e., about 0.25 mm/a (AZ91D 2.64 mm/a, 99.99% of Mg 0.20 mm/a; 1 $cm^2$:30 ml, immersion corrosion rate). Furthermore, the degradation product ($Mg^{2+}$, slightly alkaline) of the magnesium base alloy exerts an influence on the pH of the ambient environment, and is adverse to the recovery of normal tissue function, and may even trigger a hemolytic reaction. Consequently, the application of magnesium base alloys is limited in the field of medical devices. In contrast with magnesium base alloys, ferrous base alloys have a degradation rate that is too low (0.012 mm/a; 1 $cm^2$:25 ml, immersion corrosion rate) and deviate from the original design intention of degradable stents, and the degradation products ($Fe_3O_4$, $Fe_3(PO_4)_2$, etc.) may trigger calcification and inflammation. Consequently, there are no reports on successful application of ferrous stents in the cardiovascular stent field or other fields.

The degradation product ($Zn^{2+}$) of zinc does not harm the human body but is a necessary metal elements in the human body (the acceptable daily intake is about 15 mg/day), and participates in the composition of a variety of proteins and more than 300 enzyme reactions; moreover, the standard electrode potential of $Zn^{2+}$/Zn is −0.7618V, higher than the standard electrode potential of $Mg^{2+}$/Mg (−2.372V) and lower than the standard electrode potential of $Fe^{2+}$/Fe (−0.447V) or $Fe^{3+}$/Fe (−0.037V), which means the chemical activity of zinc is between the chemical activity of iron and the chemical activity of magnesium. The results of degradation tests also indicate that the degradation time of zinc is between the degradation time of magnesium and the degradation time of iron (99.95% of Fe 0.105 mm/a, 99.99% of Zn 0.325 mm/a, 99.9% of Mg 1.94 mm/a, measured with the method specified in ASTM_G31-1972).

However, pure zinc has relatively low mechanical strength and cannot be directly applied to implanted medical devices. Patent Application No. CN104587532A has disclosed a magnesium-containing zinc base alloy, which contains 0.002-4 wt % Mg, and with zinc accounting for the remaining content; in addition, the contents of other metal impurities (e.g., Fe, Al, Mn, etc.) are strictly controlled in the magnesium-containing zinc base alloy. In the patent application, magnesium is introduced into the alloy mainly for a purpose of improving the mechanical properties of zinc, but no solution to the influence of magnesium degradation on the pH of the ambient tissue environment around the implant and the possible harm to human body is provided. Patent Application No. CN103736152A has disclosed a zinc base alloy that contains Ce, Mg, Ca, and Cu. In that patent application, several metal elements are introduced into the material also for the purpose of improving the mechanical properties of zinc, but those metal elements bring uncertainties and potential safety hazards to in-vivo implantation.

Therefore, it is a key objective in the research to develop an ideal implant material that is adaptive to different positions of implantation, different environments, and different pathologic processes.

CONTENTS OF THE INVENTION

To overcome the technical drawbacks in the prior art, in a first aspect, the present invention provides a degradable zinc base alloy implant material, which, contains, by mass percentage content, 0.01 wt %-14 wt % of Fe, 0 wt %-13 wt % of functional elements, and the remainder being Zn, and preferably contains 0.5 wt %-14 wt % of Fe % of Fe and the remainder of Zn.

The functional elements include, but are not limited to, one or more of Sr, Cu, Ca, Ag, Mg, and Zr; the mass percentages of the functional elements are: Sr: 0 wt %-13 wt % (preferably 0 wt %-8 wt %), Cu: 0 wt %-13 wt % (preferably 0 wt %-5 wt %), Ca: 0 wt %-5 wt %, Ag: 0 wt %-13 wt %, Mg: 0 wt %-13 wt % %, and Zr: 0 wt %-13 wt %.

The zinc base alloy implant material contains 14 wt % of Fe, 0.01 wt %-2 wt % of Sr, and/or 0.01 wt %-3 wt % of Cu, and the remainder being Zn; and preferably contains 14 wt % of Fe, 0.01 wt %-2 wt % of Sr, 0 wt %-3 wt % of Cu, and the remainder being Zn; and more preferably contains 14 wt % of Fe, 0.1 wt %-1.5 wt % of Sr, 0.2 wt %-2 wt % of Cu, and the remainder being Zn; or further contains 0.01 wt %-5 wt % of Ca; and more preferably contains 14 wt % of Fe, 0.5 wt %-1.5 wt % of Sr, 0.1 wt %-0.5 wt % of Cu, 0.5 wt %-2 wt % of Ca, and the remainder being Zn; or further contains 0.01 wt %-13 wt % of Mg and/or Ag; more preferably contains 14 wt % of Fe, 0.1 wt %-1 wt % of Ag, and the remainder of Zn.

The zinc base alloy implant material contains 0.01 wt %-12 wt % of Fe (preferably 0.1 wt %-2 wt %), 0.01 wt %-2 wt % of functional elements, and the remainder is Zn; and preferably, the functional elements include 0.01 wt %-2 wt % of Cu; and more preferably contains 1 wt % of Fe, 1 wt % of Cu, and the remainder is Zn.

The zinc base alloy implant material contains 0.01 wt %-2 wt % of Fe (preferably 0.1 wt %-2 wt %), 0.01 wt %-2 wt % of Sr, 0 wt %-5 wt % of Ca, and the remainder is Zn; and preferably contains 0.1 wt %-1.5 wt % of Fe, 0.1 wt %-1 wt % of Sr, 0.1 wt %-1 wt % of Ca, and the remainder is Zn.

The Zn, Fe, and functional elements are at purity higher than 99.99%, and the total content of impurities is ≤0.01%.

In a second aspect, the present invention provides a method for preparing the above-mentioned zinc base alloy implant material, which contains: Zn, Fe, and functional elements mixed by mass percentage content and placed into a high-purity graphite crucible smelted, drawn, and annealed under a mixed gas atmosphere of $SF_6$ and $CO_2$, to obtain the zinc base alloy implant material.

The annealing temperature is 200° C.-500° C.

In a third aspect, the present invention provides an application of the above-mentioned zinc base alloy implant material or the zinc base alloy implant material obtained with the above-mentioned method in preparation of vascular stents, orthopedic implants, or implants in cavities and tracts, including the oesophagus, biliary tract, urethra, and the like.

In the above-mentioned application of the zinc base alloy implant material in the preparation of vascular stents, the vascular stents may be used as peripheral vascular stents and/or coronary vascular stents.

The zinc base alloy implant material contains, by mass percentage content, 14 wt % of Fe, 0.01 wt %-3.0 wt % of Cu, and the remainder is Zn.

The zinc base alloy implant material contains, by mass percentage content, 0.01 w %-2 wt % of Fe (preferably 0.1 w %-2 wt %), 0.01 wt %-2 wt % of Cu, and the remainder is Zn preferably contains 1 wt % of Fe, 1 wt % of Cu, and the remainder is Zn.

The surface of the zinc base alloy implant material is coated with anti-proliferative drug coating.

The anti-proliferative drug is paclitaxel or a derivative thereof, or rapamycin or a derivative thereof.

The drug coating is a degradable polymer layer containing the anti-proliferative drug; the degradable polymer is one or more of polylactide, poly-L-lactic acid, polylactone, polycarbonate, polyamino acid, chitosan, or sulfonated chitosan.

The vascular stent preparation method comprises: Zn, Fe, and the functional elements are mixed by mass percentage content, loading the resultant mixture into a high-purity graphite crucible, and smelted, drawn, and annealed the mixture in mixed gas atmosphere of $SF_6$ and $CO_2$, to obtain the zinc base alloy implant material in a tubular form; then treating the zinc base alloy implant material by laser engraving, polishing, spraying of drug coating, and crimping, to obtain the vascular stent.

The present invention further provides an application of the above-mentioned zinc base alloy implant material in preparation of orthopedic implants.

The zinc base alloy implant material contains, by mass percentage content, 0.01 wt %-2 wt % of Fe (preferably 0.1 wt %-2 wt %), 0.01 wt %-2 wt % of Sr, and 0 wt %-5 wt % of Ca, and preferably contains 0.1 wt %-1.5 wt % of Fe, 0.1 wt %-1 wt % of Sr, 0.1 wt %-1 wt % of Ca, and the remainder is Zn.

The zinc base alloy implant material contains, by mass percentage content, 14 wt % of Fe, 0.01 wt %-2 wt % of Sr, 0 wt %-3 wt % of Cu, and the remainder is Zn, and preferably contains 14 wt % of Fe, 0.1 wt %-1.5 wt % of Sr, 0.2 wt %-2 wt % of Cu, and the remainder is Zn.

The zinc base alloy implant material further contains, by mass percentage content, 0.1 wt %-5 wt % of Ca and preferably contains 14 wt % of Fe, 0.5 wt %-1.5 wt % of Sr, 0.1 wt %-0.5 wt % of Cu, 0.5 wt %-2 wt % of Ca, and the remainder is Zn.

The zinc base alloy implant material further contains, by mass percentage content, 0.01 wt %-13 wt % of Mg and/or Ag, and preferably contains 14 wt % of Fe, 0.1 wt %-1 wt % of Ag, and the remainder is Zn.

The orthopedic implant preparation method comprises: Zn, Fe, and the functional elements are mixed by mass percentage content and placed into a high-purity graphite crucible smelted, drawn, and annealed under mixed gas atmosphere of $SF_6$ and $CO_2$, to obtain the zinc base alloy implant material in a tubular form; then, the zinc base alloy implant material is treated by engraving and polishing to obtain the orthopedic implant.

Compared with the prior art, the present invention attains the following beneficial effects:

(1) In the present invention, iron is introduced as a main component into the zinc base alloy implant material for a purpose of forming a micro-electrode that sacrifices the anode to protect the cathode between the zinc and iron; specifically, zinc will be degraded first since the activity of iron is lower, i.e., the zinc is degraded while iron is protected, regulating the degradation rate of the zinc component;

(2) By introducing iron, the mechanical properties of the zinc base alloy implant material are significantly improved, so that the implant material is easy to process and shape, and the properties strength and plasticity, etc., meet the basic requirements of human body implant materials, such as a vascular stent, orthopedic internal fixation systems and the like;

(3) In the present invention, by introducing the functional element copper, the zinc base alloy implant material obtains the following functions:

① The degradation product $Cu^{2+}$ of copper has a certain anti-microbial effect, and can prevent biomaterial centered infection (BCI);

② The degradation product $Cu^{2+}$ of copper can promote secretion of endothelial nitric oxide synthase (eNOS) and maintain the integrity of the vascular endothelium and the functions of endothelial cells, can stimulate the secretion of vascular endothelial growth factor (VEGF), and promote the proliferation and migration of vascular endothelial cells; it can thereby promote quick re-endothelialization at the site of implantation and recovery of the normal function of vascular endothelium, and maintain and induce vascularization.

(4) In the present invention, by introducing the functional element strontium, the zinc base alloy implant material obtains the following functions:

The degradation product $Sr^{2+}$ of strontium attains an effect of promoting the function of osteoblasts and inhibiting the activity of osteoclasts, and has an outstanding osteogenesis promotion effect; in addition, the degradation product $Sr^{2+}$ can work with the degradation product $Cu^{2+}$ of copper to drive the bone reconstruction process.

(5) In the present invention, by introducing other functional elements, such as calcium, the calcification process can be promoted at special positions (e.g., at orthopedic implants), so that bodily function can be recovered better.

DETAILED DESCRIPTION OF THE EMBODIMENTS

The degradable zinc base alloy implant material provided in the present invention contains, by mass percentage content, 73 wt %-99.99 wt % Zn, 0.01 wt %-14 wt % of Fe, and 0 wt %-1-3 wt % of functional elements. The functional elements may be selected from one or more of Sr, Cu, Ca, Ag, Mg, and Zr; the mass percentages of the functional elements in the zinc base alloy implant material are: Sr: 0 wt %-13 wt % (preferably 0 wt %-8 wt %), Cu: 0 wt %-13 wt % (preferably 0 wt %-5 wt %), Ca: 0 wt %-5 wt %, Ag: 0 wt %-13 wt %, Mg: 0 wt %-13 wt %, and Zr: 0 wt %-13 wt %. Preferably, in the zinc base alloy implant material, the content of Fe is 0.01 wt %-2 wt %, the content of Cu is 0.01 wt %-2 wt %, the total content of other functional elements is <0.1 wt %, with Zn accounting for the remaining content, and the total content of impurities is <0.01 wt %. More preferably the content of Fe is 0.1 wt %-2 wt %. The Zn, Fe, and functional elements in the zinc base alloy implant material are at purity higher than 99.99%, and the total content of impurities is ≤0.01%. The inclusion of Al impurities must be avoided because Al and Fe form Fe—Al intermetallic compounds, which impact the subsequent processing (mainly polishing).

The method for preparing the degradable zinc base alloy implant material in the present invention comprises the following steps:

Zn and Fe, or Zn, Fe, and functional elements are homogeneously mixed by mass percentage content, placed into a high-purity graphite crucible, smelted, drawn, and annealed under a mixed gas atmosphere of $SF_6$ and $CO_2$ to obtain the zinc base alloy implant material. Finally, the zinc base alloy implant material is processed into a required shape.

Hereunder the present invention will be further detailed in embodiments, but those embodiments should not be understood as constituting any limitation to the present invention.

The methods used in the following embodiments are conventional methods, unless otherwise specified. The percentage values are mass percentage values, unless otherwise specified.

Embodiment 1: Zn—Fe—Cu Alloy

The degradable zinc base alloy implant material in this embodiment was a Zn—Fe—Cu alloy. Specifically, the preparation process comprised the following steps:

1) 1 wt % of Fe, 1 wt % of Cu, and the remainder was Zn (the total content of impurities was <0.001 wt %) by mass percentage content were placed into a high-purity graphite crucible, mixed, and smelted in shielding gas $SF_6$ (1 vol %) and $CO_2$, to obtain a zinc base alloy.

2) After smelting, the obtained zinc base alloy was extruded into a rod of 10 mm diameter and 50 cm length.

Figure 1:
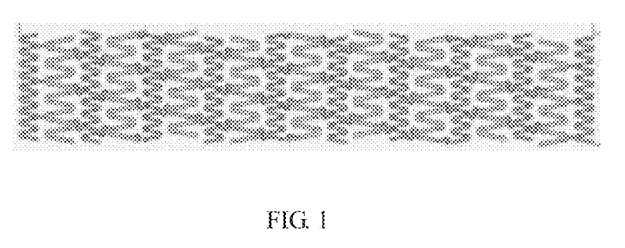
FIG. 1 is a schematic diagram of the shape of the zinc base alloy implant material in embodiment 1, which is used for a coronary vascular stent.
Figure 2:
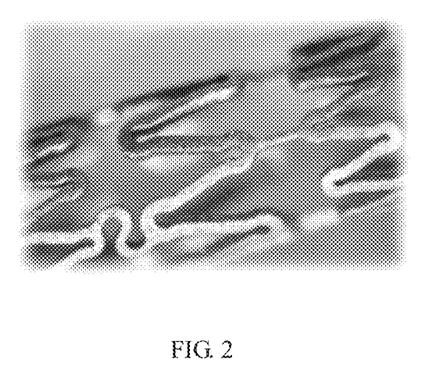
FIG. 2 is an enlarged view of the engraved pattern on the zinc base alloy implant material in the embodiment 1.

3) The obtained rod was annealed (at 200° C.-500° C. temperature, for 30 min.) and drawn several times into a tubular product with a 0.15 mm±0.013 mm outer diameter and 0.1 mm±0.013 mm wall thickness, the tubular product was designed into a stent with 3.0×20 patterns. The stent was formed by femtosecond laser engraving (the engraving patterns are shown in FIG. 1), and was polished by electrochemical polishing so that the edges and corners became smooth. Then, the stent was to be used as a coronary vascular stent. The stem width of the prepared stent was 0.1 mm, and the specific surface area of the blank portion was 20%. An enlarged view of the engraving patterns is shown in FIG. 2.

4) Finally, the surface of the stent was coated with drug coating by spraying or impregnation, and then the scaffold was crimped to a delivery system, sterilized, and packed; thus, a coronary vascular stent was obtained; the drug may be selected from rapamycin and its derivatives, or paclitaxel and its derivatives, and then coated to complete fabrication.

Effect Verification:

The zinc base alloy implant material obtained with the above-mentioned preparation method had a yield strength of about 243 MPa, a tensile strength of about 264 MPa, and a specific elongation up to 22%. It could adapt to the processing and application procedures of scaffold crimping and expansion, and was a coronary vascular stent material with ideal mechanical properties. The load bearing strength of the prepared coronary vascular stent was 1.8N after it was expanded to the nominal diameter and then compressed to 90%, and met the clinical application requirement. The degradation rate measured by the method specified in ASTM_G31-72 was 0.23 mm/a; The hemolysis characteristics were measured by the series method according to GB16886, and the hemolysis rate was 1%, which was lower than the value (5%) specified in the standard. The level of cytotoxicity was grade I, there was no intracutaneous irritation, and the sensitization ratio was 0%.

Measured in an anti-microbial performance test according to Appendix A of QB/T2591-2003 "Anti-Microbial Plastics—Test for Anti-Microbial Activity and Efficacy", the anti-microbial ratios against *Staphylococcus aureus* and *Escherichia coli* were 92% and 94% respectively, which were judged as "anti-microbial" according to Table 1 in Subsection 5.1 in the standard.

Figure 3:
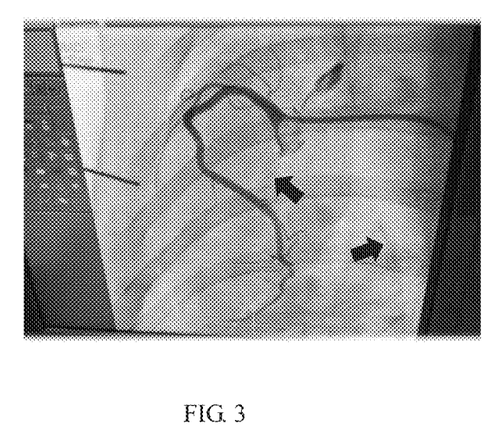
FIG. 3 is a coronary angiogram taken when the zinc base alloy implant material in the embodiment 1 is used as a vascular stent.
Figure 4:
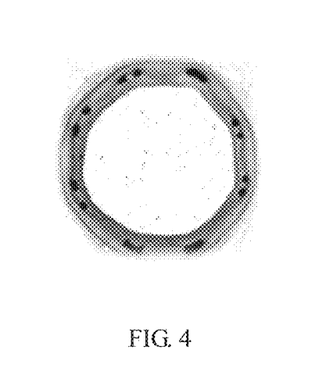
FIG. 4 is an HE stain image of a section taken when the zinc base alloy implant material in the embodiment 1 is used as a vascular stent.

The vascular stent was loaded to a delivery system and then applied in an animal model (Shanghai white pig, male, castrated, 23 kg), the result of coronary angiography and the HE staining result of a section taken after one month were observed, as shown in FIGS. 3 and 4. As seen in the figures, the zinc base alloy implant material provided in the present invention exhibited excellent development and throughput performance when it was used as a vascular stent. The result of analysis demonstrated that there was no chronic inflammation (an inducement of intermittent immunologic reactions), thrombus in the stent, or scaffold stem breakage, etc., after the vascular stent was implanted. Therefore, the zinc base alloy implant material was a degradable vascular stent material that had wide application prospects.

Embodiment 2: Zn—Fe—Cu Alloy

The degradable zinc base alloy implant material in this embodiment was a Zn—Fe—Cu alloy, which contained 0.14 wt % of Fe, 1.8 wt % of Cu, and the remainder was Zn, the total content of impurities was controlled to be <0.001 wt %, and the preparation process was the same as that in embodiment 1.

Effect Verification:

The zinc base alloy implant material obtained with the above-mentioned preparation method had an elastic modulus of 75 GPa, a yield strength of 210 MPa, and a tensile strength of 240 MPa. It could adapt to the processing and application procedures of stent crimping and expansion, and was a coronary vascular stent material with ideal mechanical properties. The degradation rate measured by the method specified in ASTM_G31-1972 was 0.19 mm/a. The hemolysis characteristics were measured by the series method according to GB16886, and the hemolysis ratio was 1%, which was lower than the value (5%) specified in the standard. The level of cytotoxicity was grade I, there was no intracutaneous irritation, and the sensitization ratio was 0%.

Embodiment 3: Zn—Fe—Sr—Ca Alloy

The degradable zinc base alloy implant material in this embodiment was a Zn—Fe—Sr—Ca alloy, which contained 0.5 wt % of Fe, 0.5 wt % of Sr, 0.5 wt % of Ca; the remainder was Zn; and the preparation process was the same as that in the embodiment 1.

Effect Verification:

The zinc base alloy implant material obtained with the above-mentioned preparation method had an elastic modulus of 80 GPa, a yield strength of 233 MPa, and a tensile strength of 270 MPa, and could meet the requirement for mechanical properties for fixation of fractured bones at load bearing positions. The degradation rate measured with the method specified in ASTM_G31-1972 was 0.38 mm/a. When tested with the methods specified in GB16886 there was no obvious cytotoxicity, intracutaneous irritation, sensitization, or genotoxicity was found. Since the elastic modulus of the zinc base alloy implant material (60~70 Gpa) was closer to the elastic modulus of cortical bones of the human body (about 20 Gpa) than conventional internal fixation materials (>100 Gpa), the zinc base alloy implant material could avoid the stress shielding effect of orthopedic implants on normal human bones, and could promote bone knitting.

Embodiment 4: Zn—Fe—Sr—Ca Alloy

The degradable zinc base alloy implant material in this embodiment was a Zn—Fe—Sr—Ca alloy, which contained 0.8 wt % of Fe, 1 wt % of Sr, 1 wt % of Ca, and the remainder is Zn.

Specifically, the preparation process comprised the following steps:

1) 0.8 wt % of Fe, 1 wt % of Sr, 1 wt % of Ca, and the remainder was Zn (the total content of impurities was <0.001 wt %) by mass percentage content were loaded into a high-purity graphite crucible and mixed and smelted in shielding gas $SF_6$ (1 vol %), to obtain a zinc base alloy.

2) After the smelting, the obtained zinc base alloy was extruded into a rod of 5 mm diameter and 50 cm length.

Figure 5:
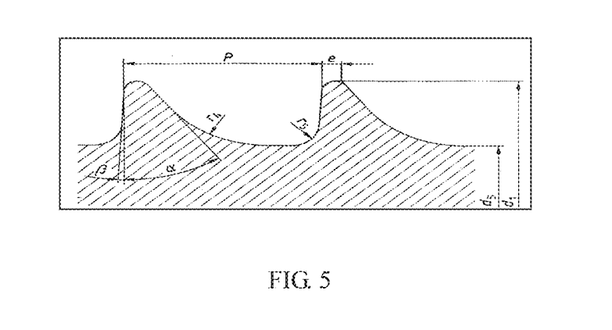
FIG. 5 is a schematic diagram of the shape of the zinc base alloy implant material in embodiment 4, which is used for an orthopedic implant.

3) The obtained rod was engraved and polished on a CNC machine tool into a straight bone nail shape as shown in FIG. 5. The dimensions were shown in Table 1.

TABLE 1

Dimensions of the Orthopedic Implant in Embodiment 1

| | Diameter | | | | | | | |
|---|---|---|---|---|---|---|---|---|
| | $d_{1-0.15}^{0}$ mm | $d_{5-0.15}^{0}$ mm | e ≈ mm | P mm | $r_4$ ≈ mm | $r_5$ ≈ mm | α ≈ ° | β ≈ ° |
| 5 mm | 2.7 | 2.1 | 0.1 | 1.0 | 0.3 | 0.05 | 35 | 3 |

Effect Verification:

The zinc base alloy implant material obtained with the above-mentioned preparation method had an elastic modulus of 64 GPa, a yield strength of 254 MPa, and a tensile strength of 270 MPa, and could meet the requirement for mechanical properties for fixation of bone fractures at load bearing positions. The degradation rate measured with the method specified in ASTM_G31-1972 was 0.30 mm/a; when tested with the methods specified in GB16886, no obvious cytotoxicity, intracutaneous irritation, sensitization, or genotoxicity was found. Since the elastic modulus of the zinc base alloy implant material (60~70 Gpa) was closer to the elastic modulus of cortical bones of human body (about 20 Gpa) than to conventional internal fixation materials (>100 Gpa), the zinc base alloy implant material could avoid the stress shielding effect of an orthopedic implants on human bones, and could promote bone knitting.

Embodiment 5: Zn—Fe Alloy

The degradable zinc base alloy implant material in this embodiment was a Zn—Fe alloy, which contained 0.14 wt % of Fe, and the remainder was Zn; the total content of impurities was <0.001 wt % and the preparation process was the same as that in embodiment 1.

Embodiment 6: Zn—Fe Alloy

The degradable zinc base alloy implant material in this embodiment was a Zn—Fe alloy, which contained 0.7 wt % of Fe, and the remainder was Zn; the total content of impurities was <0.001% and the preparation process was the same as that in embodiment 1.

Embodiment 7: Zn—Fe Alloy

The degradable zinc base alloy implant material in this embodiment was a Zn—Fe alloy, which contained 0.35 wt % of Fe, and the remainder was Zn; the total content of impurities was <0.001% and the preparation process was the same as that in embodiment 1.

Embodiment 8: Zn—Fe Alloy

The degradable zinc base alloy implant material in this embodiment was a Zn—Fe alloy, which contained 0.2 wt % of Fe, and the remainder was Zn; the total content of impurities was <0.001% and the preparation process was the same as that in embodiment 1.

Embodiment 9: Zn—Fe Alloy

The degradable zinc base alloy implant material in this embodiment was a Zn—Fe alloy, which contained 14 wt % of Fe, and the remainder was Zn; the total content of impurities was <0.001% and the preparation process was the same as that in embodiment 1.

Embodiment 10: Zn—Fe Alloy

The degradable zinc base alloy implant material in this embodiment was a Zn—Fe alloy, which contained 10 wt % of Fe, and the remainder was Zn; the total content of impurities was <0.001% and the preparation process was the same as that in embodiment 1.

Embodiment 11: Zn—Fe—Sr—Ca Alloy

The degradable zinc base alloy implant material in this embodiment was a Zn—Fe alloy, which contained 2 wt % of Fe, 2 wt % of Sr, 5 wt % of Ca, and the remainder was Zn; the total content of impurities was <0.001% and the preparation process was the same as that in embodiment 1.

Embodiment 12: Zn—Fe—Cu Alloy

The degradable zinc base alloy implant material in this embodiment was a Zn—Fe alloy, which contained 2 wt % of Fe, 2 wt % of Cu, and the remainder was Zn; the total content of impurities was <0.001% and the preparation process was the same as that in embodiment 1.

Embodiment 13: Zn—Fe Alloy

The degradable zinc base alloy implant material in this embodiment was a Zn—Fe alloy, which contained 0.5 wt % of Fe, and the remainder was Zn; the total content of impurities was <0.001% and the preparation process was the same as that in embodiment 1.

Embodiment 14: Zn—Fe—Cu Alloy

The degradable zinc base alloy implant material in this embodiment was a Zn—Fe—Cu alloy, which contained 2.0 wt % of Fe, 0.1 wt % of Cu, and the remainder was Zn; the total content of impurities was <0.001 wt % and the preparation process was the same as that in embodiment 1.

Embodiment 15: Zn—Fe—Cu Alloy

The degradable zinc base alloy implant material in this embodiment was a Zn—Fe—Cu alloy, which contained 10.0 wt % of Fe, 2.0 wt % of Cu, and the remainder was Zn; the total content of impurities was <0.001 wt % and the preparation process was the same as that in embodiment 1.

Embodiment 16: Zn—Fe—Cu Alloy

The degradable zinc base alloy implant material in this embodiment was a Zn—Fe—Cu alloy, which contained 12.0 wt % of Fe, 3.0 wt % of Cu, and the remainder was Zn; the total content of impurities was <0.001 wt % and the preparation process was the same as that in embodiment 1.

Embodiment 17: Zn—Fe—Cu Alloy

The degradable zinc base alloy implant material in this embodiment was a Zn—Fe—Cu alloy, which contained 5.0 wt % of Fe, 3.0 wt % of Cu, and the remainder was Zn; the total content of impurities was <0.001 wt % and the preparation process was the same as that in embodiment 1.

Embodiment 18: Zn—Fe—Cu—Sr Alloy

The degradable zinc base alloy implant material in this embodiment was a Zn—Fe—Cu—Sr alloy, which contained 14 wt % of Fe, 1.8 wt % of Cu, 1 wt % of Sr, and the remainder was Zn; the total content of impurities was <0.001 wt % and the preparation process was the same as that in embodiment 4.

Embodiment 19: Zn—Fe—Cu—Sr—Ca Alloy

The degradable zinc base alloy implant material in this embodiment was a Zn—Fe—Cu—Sr—Ca alloy, which contained 14 wt % of Fe, 0.2 wt % of Cu, 1 wt % of Sr, 1 wt % of Ca, and the remainder was Zn; the total content of impurities was <0.001 wt % and the preparation process was the same as that in embodiment 4.

Embodiment 20: Zn—Fe—Ag Alloy

The degradable zinc base alloy implant material in this embodiment was a Zn—Fe—Ag alloy, which contained 14 wt % of Fe, 0.5 wt % of Ag, and the remainder was Zn; the total content of impurities was <0.001 wt % and the preparation process was the same as that in embodiment 4.

Reference example 1 (Zn—Fe—Cu alloy with Fe content higher than 14%): a zinc base alloy implant material was obtained with the preparation method disclosed in the present invention, wherein, the zinc base alloy implant material contained 16 wt % of Fe, 1 wt % of Cu, and the remainder was Zn.

Reference example 2 (Zn—Cu alloy with Fe content lower than 0.1%): a zinc base alloy implant material was obtained with the preparation method disclosed in the present invention, wherein, the zinc base alloy implant material contained 1 wt % of Cu, 0.001 wt % of Fe, and the remainder was Zn.

Reference example 3 (Zn—Fe—Cu alloy with the content of functional components (Cu) higher than 13%): a zinc base alloy implant material was obtained with the preparation method disclosed in the present invention, wherein, the zinc base alloy implant material contained 14 wt % of Cu, 1 wt % of Fe, and the remainder was Zn.

Reference example 4 (Zn—Fe—Cu—Sr—Ca alloy with Fe content higher than 14%): a zinc base alloy implant material was obtained with the preparation method disclosed in the present invention, wherein, the zinc base alloy implant material contained 16 wt % of Fe, 1 wt % of Cu, 8 wt % of Sr, 8 wt % of Ca, and the remainder was Zn.

Reference example 5 (zinc base alloy without Fe in the prior art): a zinc base alloy implant material was obtained with the preparation method disclosed in Patent Application No. CN103736152A, wherein, the zinc base alloy implant material contained 0.1 wt % Ce, 0.5 wt % of Mg, 0.1 wt % of Ca, 1.5 wt % of Cu, and the remainder was Zn.

Reference example 6 (Zn—Fe alloy with Fe content higher than 14%): a zinc base alloy implant material was obtained with the preparation method disclosed in the present invention, wherein, the zinc base alloy implant material contained 17 wt % of Fe, and the remainder was Zn.

Reference example 7 (zinc material without Fe): a zinc base alloy implant material was obtained with the preparation method disclosed in the present invention, wherein, the zinc base alloy implant material only contained Zn and 1 wt % of Cu, without any other elements.

The zinc base alloy implant materials obtained in the embodiments 1-20 were fabricated for use in vascular stents, orthopedic implants, or degradable implants in the oesophagus, biliary tract, urethra, or other cavities or tracts. The mechanical properties and corrosion resistance property ((ASTM-G31-72), Hank's simulated body fluid, 37° C.) of the zinc base alloy implant materials are shown in Table 2. The mechanical properties and corrosion resistance property of the zinc base alloy implant materials obtained in the reference examples 1-7 are also shown in Table 2.

TABLE 2

Mechanical Properties and Corrosion Resistance Property of the Implant Materials in Embodiments 1-20 and Reference Examples 1-7

| Embodiment | Yield strength, MPa | Tensile strength, MPa | Elastic modulus, GPa | Specific elongation, % | Corrosion rate |
|---|---|---|---|---|---|
| Embodiment 1 | 243 | 264 | 70 | 22 | 0.23 mm/a |
| Embodiment 2 | 210 | 240 | 75 | 12 | 0.19 mm/a |
| Embodiment 3 | 233 | 270 | 80 | 12 | 0.38 mm/a |
| Embodiment 4 | 254 | 270 | 64 | 20 | 0.30 mm/a |
| Embodiment 5 | 215 | 242 | 78 | 22 | 0.20 mm/a |
| Embodiment 6 | 200 | 270 | 76 | 18 | 0.26 mm/a |
| Embodiment 7 | 202 | 234 | 82 | 16 | 0.28 mm/a |
| Embodiment 8 | 243 | 267 | 77 | 24 | 0.18 mm/a |
| Embodiment 9 | 156 | 172 | 83 | 12 | 0.20 mm/a |
| Embodiment 10 | 165 | 188 | 80 | 13 | 0.24 mm/a |
| Embodiment 11 | 214 | 232 | 85 | 13 | 0.33 mm/a |
| Embodiment 12 | 207 | 219 | 77 | 17 | 0.42 mm/a |
| Embodiment 13 | 205 | 249 | 72 | 16 | 0.45 mm/a |
| Embodiment 14 | 203 | 222 | 80 | 17 | 0.31 mm/a |
| Embodiment 15 | 189 | 234 | 83 | 12 | 0.20 mm/a |
| Embodiment 16 | 183 | 234 | 82 | 18 | 0.22 mm/a |
| Embodiment 17 | 177 | 190 | 77 | 16 | 0.20 mm/a |
| Embodiment 18 | 218 | 268 | 74 | 13 | 0.18 mm/a |
| Embodiment 19 | 223 | 243 | 66 | 8 | 0.20 mm/a |
| Embodiment 20 | 169 | 188 | 71 | 14 | 0.21 mm/a |
| Reference Example 1 | 200 | 266 | 89 | 8 | 0.17 mm/a |
| Reference Example 2 | 30 | 60 | 77 | 3 | 0.32 mm/a |
| Reference Example 3 | 202 | 241 | 76 | 25 | 0.09 mm/a |

TABLE 2-continued

Mechanical Properties and Corrosion Resistance Property of the Implant
Materials in Embodiments 1-20 and Reference Examples 1-7

| Embodiment | Yield strength, MPa | Tensile strength, MPa | Elastic modulus, GPa | Specific elongation, % | Corrosion rate |
|---|---|---|---|---|---|
| Reference Example 4 | 229 | 249 | 92 | 5 | 0.11 mm/a |
| Reference Example 5 | 221 | 234 | 77 | 4 | 0.15 mm/a |
| Reference Example 6 | 207 | 256 | 70 | 3 | 0.08 mm/a |
| Reference Example 7 | 179 | 224 | 65 | 11 | 0.08 mm/a |

The results in Table 2 indicated that the mechanical strength (yield strength and tensile strength), elastic property (elastic modulus), and extensibility (specific elongation) of the degradable zinc base alloy implant material provided in the present invention met the requirements for load bearing capacity and processability of implanted stents. In addition, the degradation rate (corrosion rate) of the material was ideal (0.15 mm/a-0.45 mm/a), and the material could be used as a degradable in-vivo implant material. Tested with the method specified in ISO10993, the materials in the embodiments 1-20 had grade II cytotoxicity (i.e., no obvious cytotoxicity), to not cause any intracutaneous irritation or sensitization, and had no genotoxicity.

Compared with the zinc base alloy implant material provided in the present invention, the materials in the reference examples 1-7 had mechanical strength that was too low (e.g., in the reference example 2) for them to be used as implants that must meet a specific load bearing capacity requirements; or they had an elastic modulus that had an excessively high difference from the elastic modulus of human bones (e.g., in reference examples 1 and 4), causing a stress shielding effect that may result in side effects such as delayed bone knitting and mismatch effects, etc.; or they had a degradation rate that was too low (e.g., in reference examples 3, 4, 6 and 7) for them to meet the clinical requirement for material degradation; or they had extremely low specific elongation (<10%), resulting in excessively high material brittleness (e.g., in reference examples 1, 2, and 4-6), poor processability, high frangibility, and application risks and inconvenience.

INDUSTRIAL APPLICABILITY

The degradable zinc base alloy implant material provided in the present invention increases the degradation rate of the zinc component by forming a micro-electrode between the zinc and iron, has significantly improved mechanical properties so that it can be easily processed and shaped, and has strength and plasticity property that meet the basic requirements for implanted materials in human body, such as vascular stents and orthopedic internal fixation systems, etc. Therefore, the degradable zinc base alloy implant material provided in the present invention is suitable for industrial application.

The invention claimed is:
1. A degradable zinc base alloy implant material consisting of 14 wt % of Fe, 1.8 wt % Cu, 1 wt % Sr, and remainder being Zn.
2. The zinc base alloy implant material according to claim 1, wherein the Zn, Fe, Cu, and Sr are at purity higher than 99.99%, and the total content of impurities of the base alloy is ≤0.01%.

* * * * *